US010898318B2

(12) United States Patent
Dagsland

(10) Patent No.: US 10,898,318 B2
(45) Date of Patent: Jan. 26, 2021

(54) METHOD AND DEVICE FOR SECURELY LOADING AND MOUNTING A TUBULAR DEVICE IN A FLEXIBLE WALL

(71) Applicant: Atos Medical AB, Horby (SE)

(72) Inventor: Allan Dagsland, Kristianstad (SE)

(73) Assignee: Atos Medical AB (*) Notice: Subject to any disclaimer, the term of this patent is extended or adjusted under 35 U.S.C. 154(b) by 264 days.

(21) Appl. No.: 15/780,634

(22) PCT Filed: Nov. 30, 2016

(86) PCT No.: PCT/SE2016/051190
§ 371 (c)(1),
(2) Date: May 31, 2018

(87) PCT Pub. No.: WO2017/095311
PCT Pub. Date: Jun. 8, 2017

(65) Prior Publication Data
US 2018/0353290 A1 Dec. 13, 2018

(30) Foreign Application Priority Data

Dec. 2, 2015 (SE) ........................ 1551577
Feb. 12, 2016 (SE) ........................ 1650180

(51) Int. Cl.
*A61F 2/20* (2006.01)
*B25B 27/28* (2006.01)
(Continued)

(52) U.S. Cl.
CPC .............. *A61F 2/203* (2013.01); *B25B 27/28* (2013.01); *A61F 2/0095* (2013.01); *A61F 2/9522* (2020.05); *A61F 2002/9505* (2013.01)

(58) Field of Classification Search
CPC .......... A61F 2/203; A61F 2/0095; A61F 2/20; A61F 2/9505; A61F 2/9522; B25B 27/28
(Continued)

(56) References Cited

U.S. PATENT DOCUMENTS 4,927,185 A  5/1990 McNaughton
5,300,119 A  4/1994 Blom
(Continued)

FOREIGN PATENT DOCUMENTS

CN  102006904 A  4/2011
CN  104080411 A  10/2014
(Continued)

OTHER PUBLICATIONS

EP Search Report for EP16871153.9, dated Jul. 5, 2019.
Chinese Office Action dated Apr. 23, 2020 related to corresponding Chinese Patent Application No. 201680070426.1.

*Primary Examiner* — Suba Ganesan
*Assistant Examiner* — Aren Patel
(74) *Attorney, Agent, or Firm* — Fishman Stewart PLLC

(57) ABSTRACT

A loading device for inserting a bushing into a through-aperture in a flexible wall or a cap, said bushing having flanges projecting transversely at each end thereof, said flanges being resiliently foldable towards the longitudinal axis of said bushing, said loading device comprising: an inserter rod, a pincher and a loading. When the inserter is pushed distally in an insertion direction, the bushing is forced towards the loading tube which will receive the bushing therein with said flanges folded and projecting substantially axially.

16 Claims, 11 Drawing Sheets

(51) Int. Cl.
*A61F 2/00* (2006.01)
*A61F 2/95* (2013.01)

(58) Field of Classification Search
USPC .............................................................. 623/9
See application file for complete search history.

(56) References Cited

U.S. PATENT DOCUMENTS

| | | | |
|---|---|---|---|
| 5,976,151 A | 11/1999 | Siegbahn | |
| 2008/0149107 A1 | 6/2008 | Byatt | |
| 2009/0036983 A1* | 2/2009 | Tran | A61F 2/203 |
| | | | 623/9 |
| 2009/0102180 A1* | 4/2009 | Karling | A61F 2/203 |
| | | | 285/20 |
| 2011/0190862 A1* | 8/2011 | Bashiri | A61F 2/95 |
| | | | 623/1.11 |
| 2014/0379065 A1* | 12/2014 | Johnson | A61F 2/958 |
| | | | 623/1.11 |
| 2017/0216068 A1* | 8/2017 | Dwyer | A61F 2/966 |

FOREIGN PATENT DOCUMENTS

| | | | |
|---|---|---|---|
| CN | 104144724 A | 11/2014 | |
| EP | 0137528 A1 | 4/1985 | |
| EP | 0868291 A1 | 10/1998 | |
| WO | WO-9217117 A1 | 10/1992 | |
| WO | WO-2005097001 A1 | 10/2005 | |
| WO | 2015107320 A1 | 7/2015 | |

\* cited by examiner

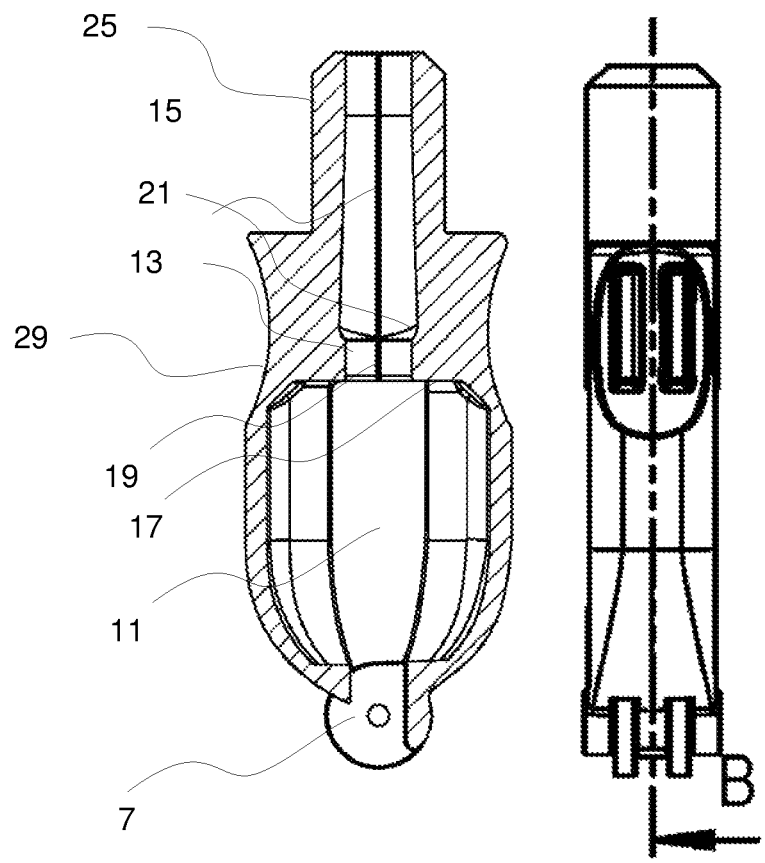
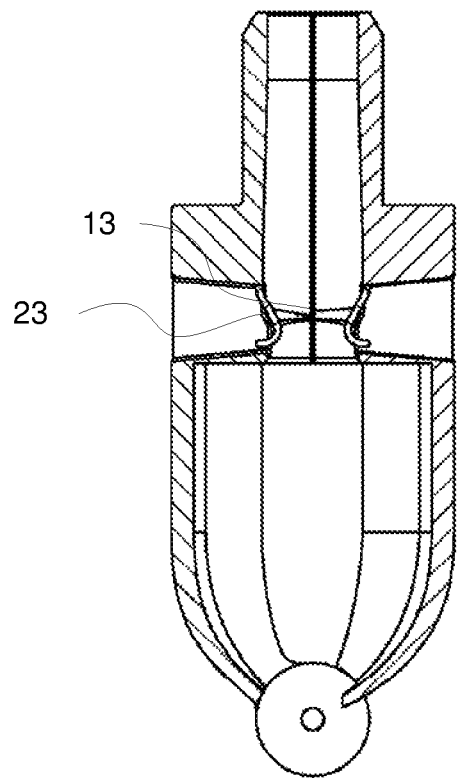
Figure 9
Figure 10

METHOD AND DEVICE FOR SECURELY LOADING AND MOUNTING A TUBULAR DEVICE IN A FLEXIBLE WALL

CROSS REFERENCE TO RELATED APPLICATIONS

This application claims priority to International Application PCT/SE2016/051190 filed on Nov. 30, 2016, Swedish Application SE 1650180-1 filed on Feb. 12, 2016 and Swedish Application SE 1551577-8 filed on Dec. 2, 2015, the contents of each of which are hereby incorporated by reference in their entirety.

FIELD OF THE INVENTION

This invention pertains in general to a method and a device for inserting a tubular element having a retainer projecting transversely at each end thereof, said retainer being resiliently foldable towards the axis of said tubular element, into through aperture in a wall accessible from one side only.

BACKGROUND OF THE INVENTION

There may be a need of mounting in products of flexible material, such as inflatable objects, or hoses of coated fabric or rubber material, tubular elements of different kinds for example bushings, connectors, or valves, in a flexible wall which is accessible from one side only.

EP-B1-0868291 discloses a method and device for mounting a tubular element in a flexible wall using a loading tube and a tool inserted therein supporting the tubular element during delivery through the loading tube.

Although the method and device are well proven for use by professionally trained personal, the method and device may be improved for less trained operators. There is a need for improving the insertion of the tubular device into a loading tube. Especially, the reliability and convenience of bending retainers into an axially orientation, from initially projecting transversely, at each end of the tubular device when pushing the device into a loading tube may be improved. This step is hitherto performed manually by an operator of the loading tube, wherein this step, likewise all manually performed operations, underlies fluctuations in reliability of the step performed.

Potential sources of errors are for instance the orientation of the retainers when loaded into the loading tube, the rotational orientation of the tubular device in the loading tube and thus in the flexible wall when mounted into the wall, or contamination of the tubular device with undesired contaminants. There is also a need for such a loading device and method being operable by a more simple manipulation of a smart inserting device, for instance a one-hand operation.

Hence, an improved mounting device would be advantageous. The purpose of the invention is to facilitate such mounting of a tubular device and to improve the ease-of-use of a loading device used for said mounting, as well as improving the security and reliability of the mounting.

SUMMARY OF THE INVENTION

Accordingly, the present invention preferably seeks to mitigate, alleviate or eliminate one or more of the above-identified deficiencies in the art and disadvantages singly or in any combination and solves at least the above mentioned problems by providing a loading device for inserting a bushing into a through-aperture in a flexible wall or a cap. The bushing may have flanges projecting transversely at each end thereof, and said flanges being resiliently foldable towards the longitudinal axis of said bushing. The loading device comprises an inserter rod, and a pincher. The inserter comprises a distal bushing seat onto which the bushing can be mounted. The pincher comprises a first pincher half and a second pincher half, connected to each other at a hinge joint, where the first and the second halves can be pivoted between an open and closed position, and in a closed position form an introduction section, a bending section and a loading section for the bushing on the inside of the first and second halves. The pincher, mounted on the inserter, will bend the flanges projecting transversely at each end of the bushing towards the longitudinal axis of a bushing mounted on the inserter, when the first and second halves are pivoted from an open to a closed configuration. When the inserter is pushed distally in an insertion direction, the bushing is forced towards the loading section which will receive the bushing therein with said flanges folded and projecting substantially axially.

The loading device may further comprise a loading tube, wherein the pincher comprises a tube mount for receiving the loading tube on the outside of the closed halves, such that when the inserter is pushed distally in an insertion direction, the bushing is forced towards the loading tube which will receive the bushing therein with said flanges folded and projecting substantially axially.

BRIEF DESCRIPTION OF THE DRAWINGS

These and other aspects, features and advantages of which the invention is capable of will be apparent and elucidated from the following description of embodiments of the present invention, reference being made to the accompanying drawings, in which

FIG. 9 shows one cross-sectional view and one side view of a pincher in a closed configuration according to one embodiment of the invention;

FIG. 10 shows one cross-sectional view of a pincher with a spring in a closed configuration according to one embodiment of the invention;

DESCRIPTION OF EMBODIMENTS

Figure 1:
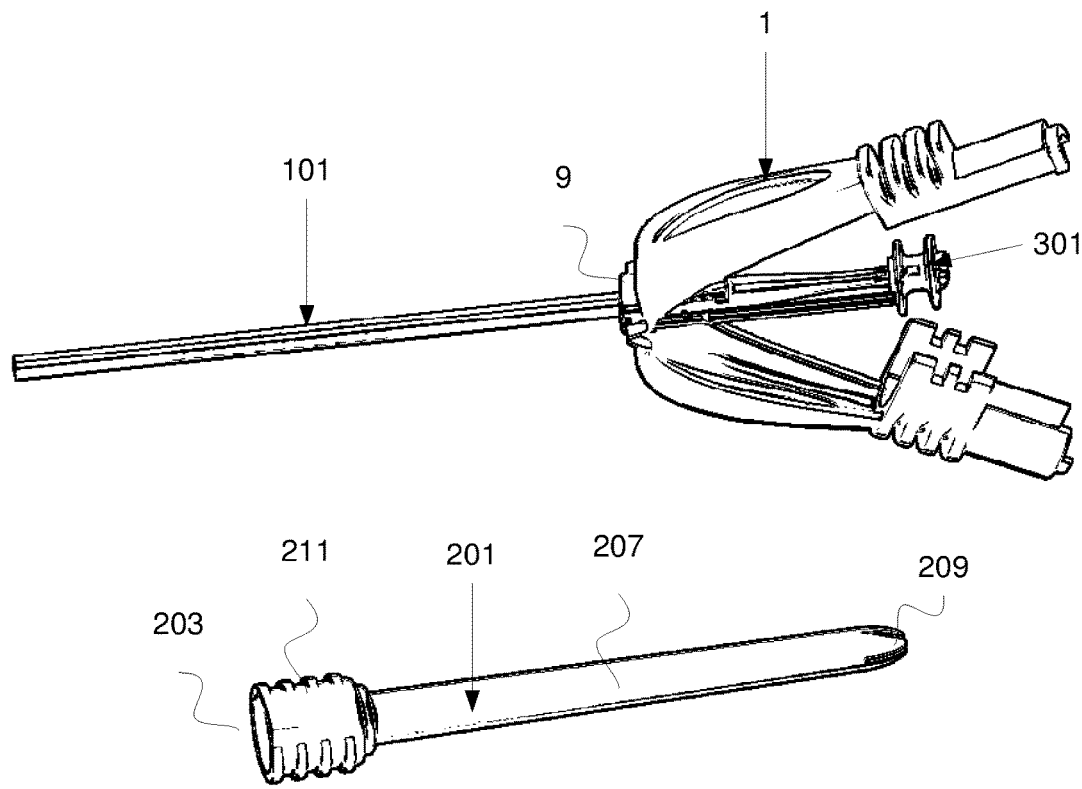
FIG. 1 is a schematic representation illustrating the components of a loading device according to an embodiment of the invention, comprising an inserter where a bushing is mounted, a pincher, and a loading tube.
Figure 2:
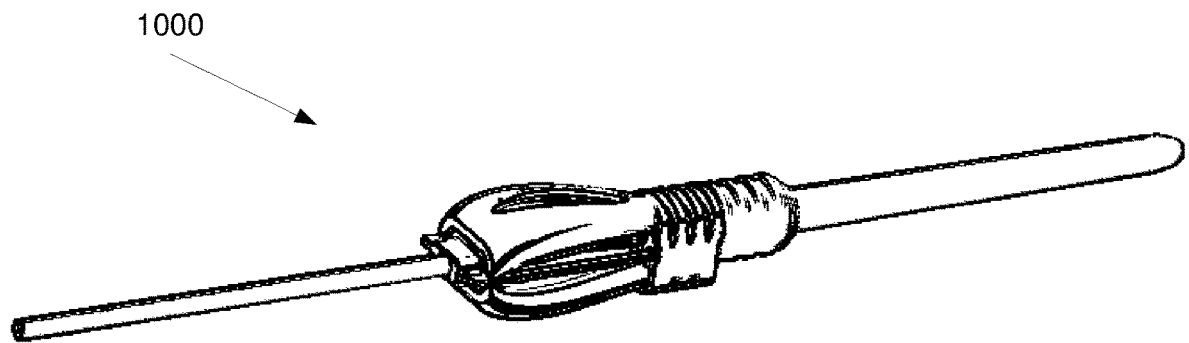
FIG. 2 is a schematic representation illustrating a loading device in closed configuration according to an embodiment of the invention.

In FIGS. 1 and 2 the components of a loading device 1000 for loading a bushing 301, such as a voice prosthesis, according to a first embodiment for practising a method according to the invention is shown.

The loading device 1000 is a tool for inserting a bushing 301 into a flexible wall, comprising: an inserter 101 constructed as an elongate shank or rod; a pincher 1, which folds in over the bushing 301. The loading device can also comprise a loading tube 201, which mounts on the pincher 1. All parts are preferably made of plastic material. The bushing 301 may however comprise metal parts, such as a metal central tube element, and rubber or silicone parts, such as retaining flanges.

As can be seen in FIG. 1, the bushing 301 can be mounted on the inserter 101. Also, the pincher 1 may be mounted on the inserter 101. When the pincher is in closed configuration, the loading tube 201 can be mounted on the pincher 1. In FIG. 1, the pincher 1 is in open configuration and the loading tube 201 is un-mounted. In FIG. 2, the pincher 1 is in closed configuration, mounted over the bushing 301 and the inserter 101. In this configuration, the loading tube 201 can be mounted on the pincher 1, as seen in FIG. 2.

Figure 3:
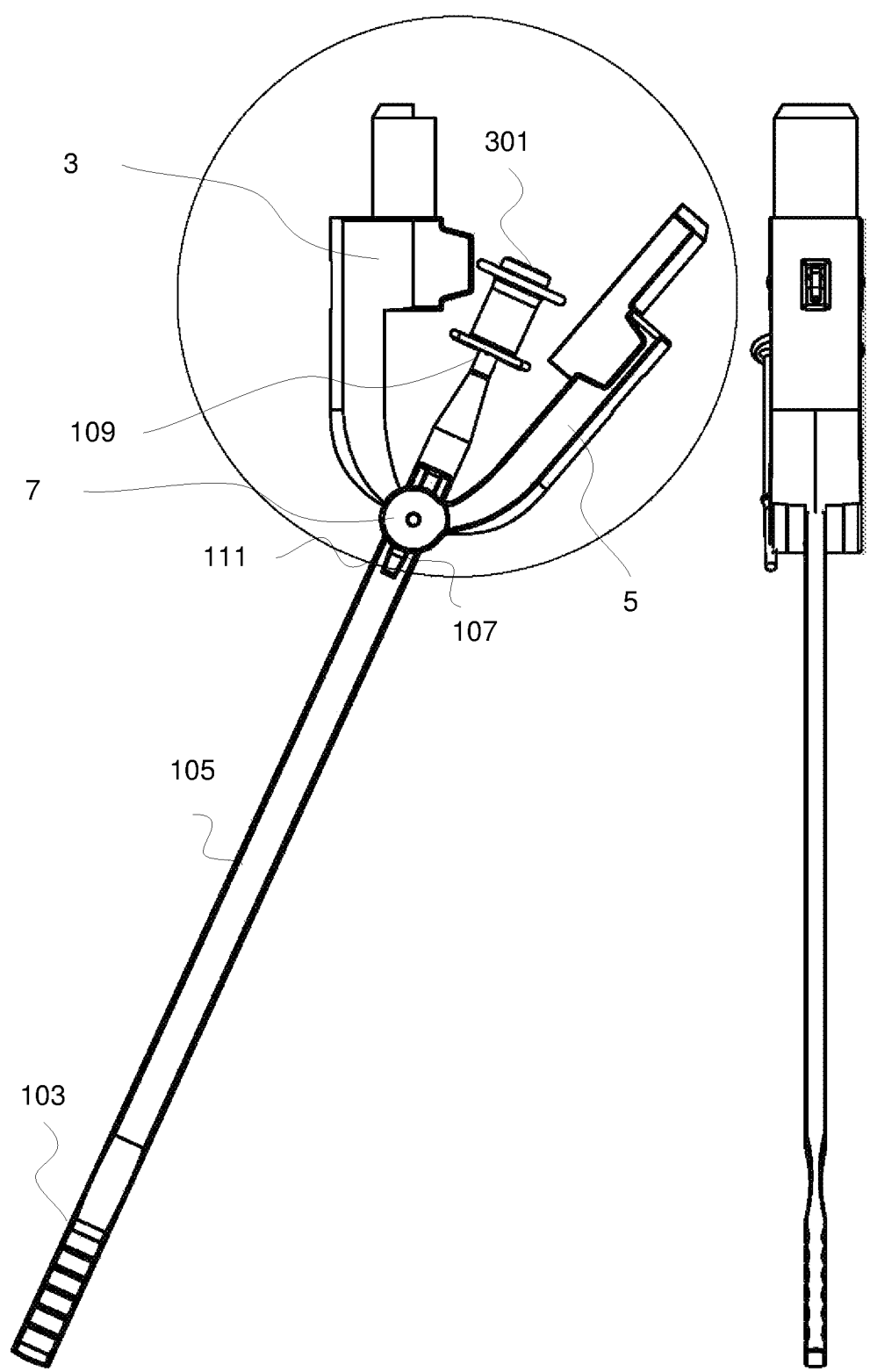
FIG. 3 shows two side views drawings, illustrating an inserter where a bushing is mounted, and a pincher in open configuration.

As can be seen in FIG. 3, the inserter 101 comprises a proximal handle portion 103, a central shank portion 105, a distal groove portion 107, for mounting the pincher 1, and a bushing seat 109, for receiving the bushing 301 at the distal end opposite to the handle portion 103.

The handle portion 103 may comprise a high friction surface, such as a ribbed, crinkled, corrugated, jagged or toothed surface, adapted for applying an axial force when pushing the inserter 101 into the loading tube 201. The inserter 101 is rod shaped. It may have different cross-sectional geometries, such as, but not limited to, a cylindrical, squared or rectangular shape. The inserter may also have different geometry in different sections, such as having a cylindrical handle portion 103 and bushing seat 109, while the shank portion 105 and groove portion 107 may be rectangular. Benefits of different geometries include that a rectangular groove portion 107 may help to orient and stabilise a mounted pincher 1, as can be seen in FIGS. 4 and 5, while a circular handle portion 103 may be more comfortable to grip.

The groove portion 107 may comprise a through hole 111 through the inserter 101, perpendicular to the length axis of the inserter 101, for arranging the pincher 1 to be cooperating with the groove portion 107 and/or through hole 111 in a retaining manner, whereby correct position of the pincher 1 in relation to the inserter 101 and the bushing 301, for subsequent distal displacement of the bushing through the use of the inserter 101, may be allowed. The hole 111 may be elongated, to allow a mounted pincher 1 to be moved in the proximal direction towards the handle portion 103 of the inserter 101 or in the distal direction of the inserter 101, within the confides of the hole 111. The bushing seat 109 is in the form of a cylindrical head 113. The cylindrical head 113 may be slanting forward, for facilitating insertion of the bushing seat 109 into bushing 301. This bushing seat 109 is adapted for receiving for example a bushing 301, such as a voice prosthesis, thereon, whereby the bushing seat 109 is adapted in size and shape for cooperation with the lumen of a voice prosthesis on the end of the voice prosthesis not carrying the voice prosthesis valve flap.

Figure 4:
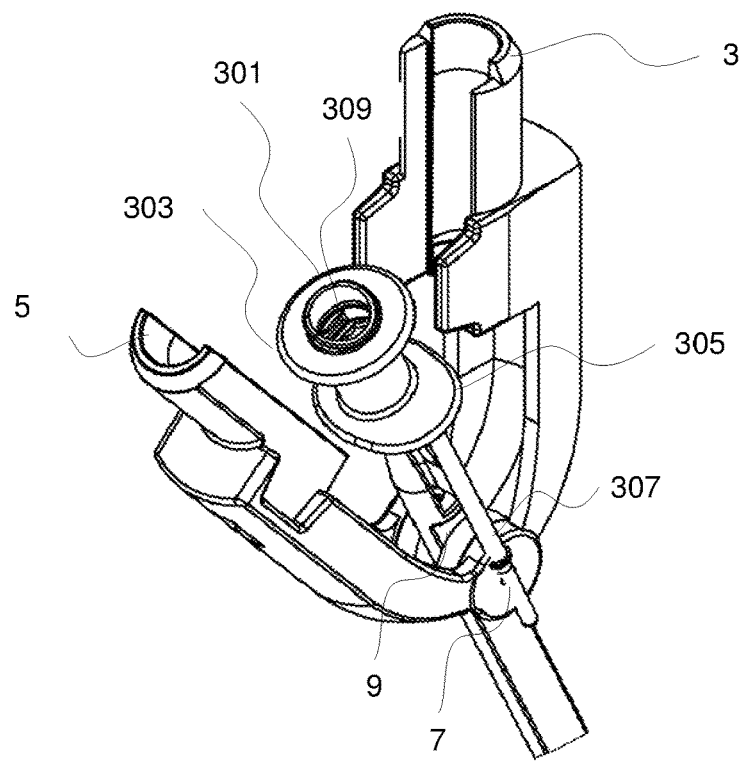
FIG. 4 shows a schematic representation, illustrating an inserter where a bushing is mounted, and a pincher in open configuration.
Figure 5:
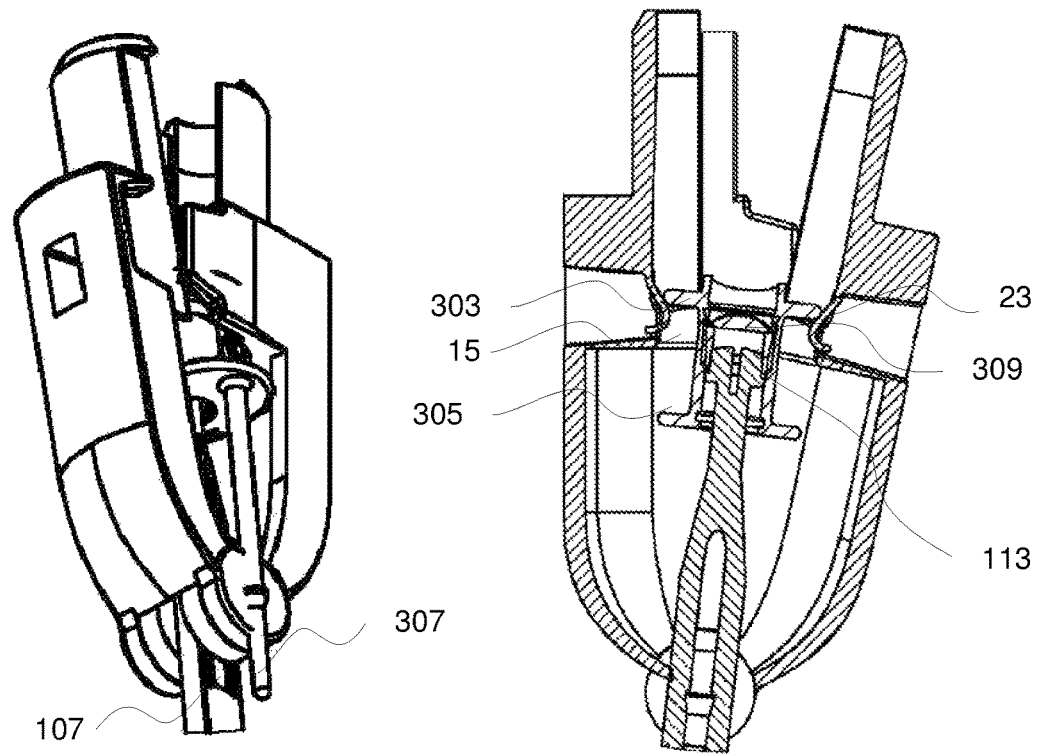
FIG. 5 shows one schematic representation and one cross-sectional view, illustrating an inserter where a bushing is mounted, and a pincher in half-open configuration.
Figure 6:
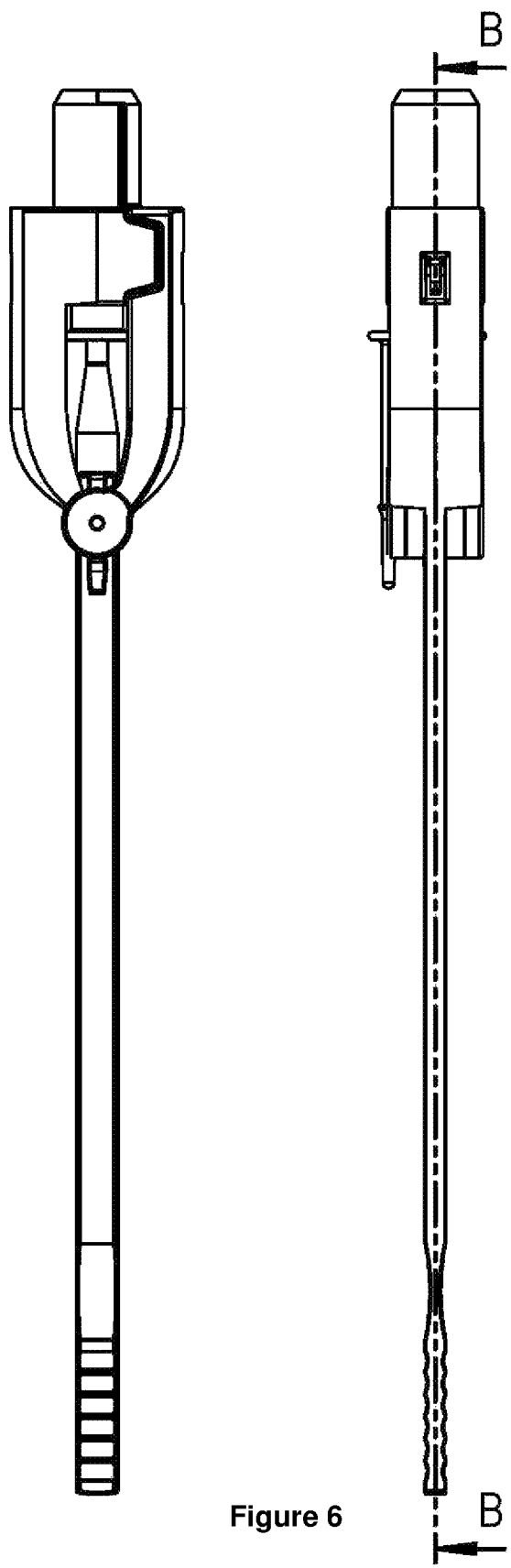
FIG. 6 shows two side views drawings, illustrating an inserter where a bushing is mounted, and a pincher in closed configuration.

As can be seen in FIGS. 3 and 4, the pincher 1 comprises a first half 3 and a second half 5, connected to each other at a hinge joint 7. The first half 3 and the second half 5 may be two sides of a solid object linked at the hinge joint 7, or two separate pieces mounted together at the hinge joint 7.

The hinge joint 7 may also function as a connector to the groove portion 107 of the inserter 101, such as for mounting through a hole 111 in the inserter 101, as can be seen in FIG. 3. The hinge joint 7 may then carry an inwardly extending protrusion 8, extending one or each side of the groove portion 107, for guiding the pincher 1 and asserting right position for pincher 1 from which the pincher 1 will fold flanges on the bushing 301 in the correct way. The hinge joint 7 may likewise comprise a passage 9, through which the inserter 101 may run when mounted, as seen in FIGS. 1, 2 and 3.

Figure 7:
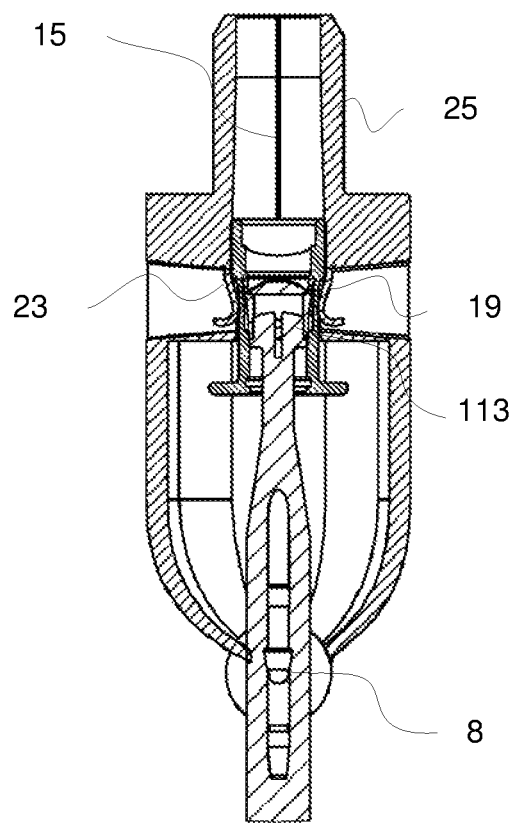
FIG. 7 shows a cross-sectional detailed view, illustrating part of an inserter where a bushing is mounted, and a pincher in closed configuration.

The two halves 3, 5 may be pivoted towards or away from each other, through rotation around the hinge joint, between a closed and open position, respectively. FIG. 3 shows the open configuration, while FIG. 7 shows the closed configuration.

When in closed configuration, as can be seen in FIG. 9, the two halves form introduction section 11, a bending section 13 and a loading section 15 for the bushing 301.

The introduction section 11 is the section closest to the hinge joint 7, while the loading section 15 is furthest away from the hinge joint 7, with the bending section 13 in-between the introduction section 11 and the loading section 15.

The introduction section 11 comprises a compartment towards the hinge joint 7 end and a wall 17 with a central axial passage 19 for receiving the bushing 301 towards the loading section 15 end.

The bending section 13 comprises a central axis passage 19 with a diameter similar to that of the central section between flanges 303, 305 of the bushing 301. The bending section 13 may have a tapered section 21 with a smaller inside diameter in the direction towards the introduction section 11 and a larger inside diameter at the loading section 15 end of bending section 13, as can be seen in FIG. 9. Alternatively, the bending section 13 comprises springs 23 forming the walls of the bending section 13. The springs 23 preferably hinge around a connection point at the load section 15 end of the bending section, making it taper conically from a smaller inside diameter to a larger inside diameter at the loading section 15 end of bending section 13, as can be seen in FIG. 9. The angle of the tapered section 21 or springs 23 facilitates easier bending of the flanges 303 of the bushing 301 by steering the bending of the flange 303 of a mounted bushing 301 to the correct bending direction.

The loading section 15 has a central through-hole, with a diameter similar to that of the inside diameter of the introduction section 203 of the loading tube 201. When the loading tube 201 is mounted on the pincher 1, a continuous connection is formed from the loading section to the loading tube. If a loading tube is not used, the loading section may be used directly for delivery of the bushing into the an aperture in a flexible wall.

Part of the outer surface of the loading section 15 is a smooth cylindrical surface which functions as a tube mount 25 for the loading tube 201. Once the pincher is in closed position, the loading tube can easily be slid over the pincher 1 tube mount 25, as can be seen in FIG. 2. Adjacent to the tube mount 25 is a handle area 29, one on each half 3, 5 of the pincher 1, for maneuvering the two halves 3, 5 between open and closed position, and for holding the pincher 1 stationary in a closed position during loading.

Figure 8:
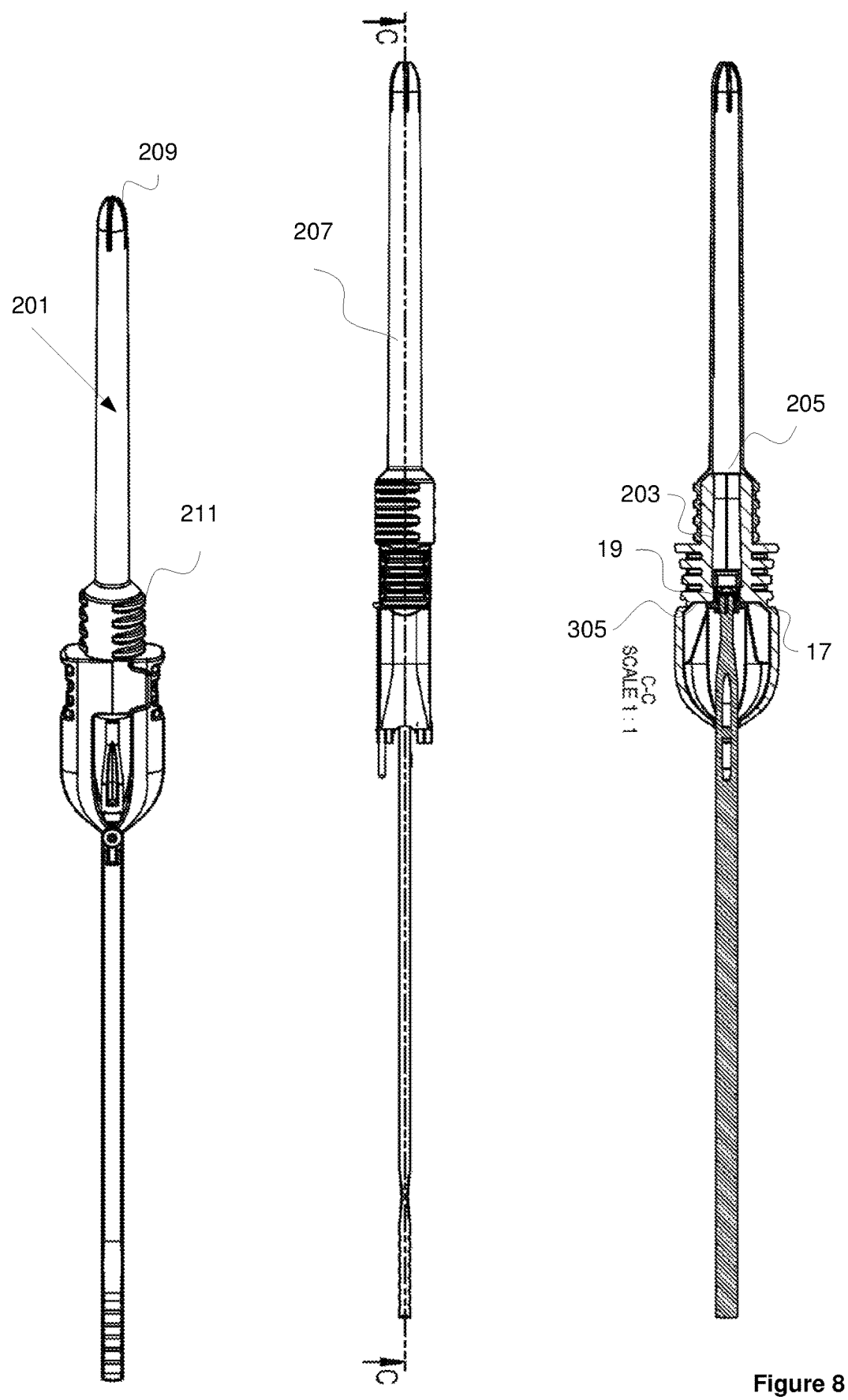
FIG. 8 shows one schematic representation, one side drawing and one cross-sectional view of a loading device according to an embodiment of the invention, comprising an inserter where a bushing is mounted, a pincher in closed configuration, and a loading tube.
Figure 11:
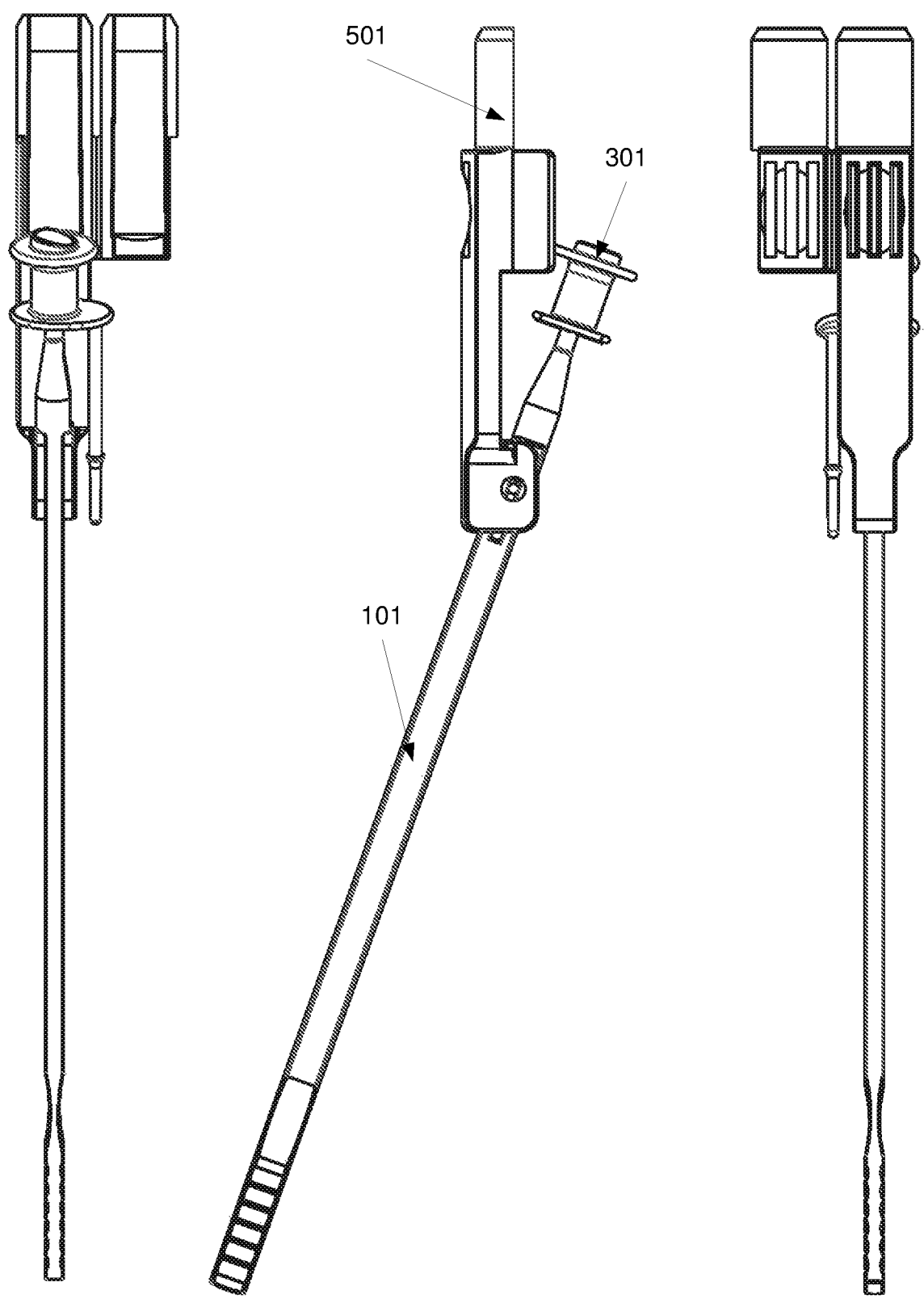
FIG. 11 shows three schematic representations illustrating a loading device in open configuration according to an embodiment of the invention, comprising an inserter where a bushing is mounted, and a pincher.

As can be seen in FIG. 8, the loading tube 201 comprises a mount section 203 which fits on the tube mount 25 of a closed pincher 1, an introduction section 205 where the bushing 301 can be inserted, an elongated section 207 ending in a delivery section 209. At the end opposite to the delivery section 203, two gripping appliances 211 are arranged transversally on the outer surface of the loading tube 201. The delivery section 209 of loading tube 201 may have a cylindrical lumen but preferably the lumen thereof tapers conically from a larger inside diameter at the end of the loading tube adjacent to introduction section 205, to a smaller inside diameter at the delivery section 209 end of the loading tube 201. This facilitates easier interaction or insertion of the loading tube 201 delivery section 209 into an aperture in a flexible wall.

The bushing 301 that is to be inserted into the loading section 215 or loading tube 201 and to be mounted in a flexible wall by the method according to the invention and by using the loading device 1000 described, is cylindrically tubular and forms a central passage. As can be seen in FIGS. 4 and 5, the bushing 301 has at each end a flange 303 and 305, respectively, integral with the rest of the bushing 1. The anchoring security string 307 is formed as a tail integral with flange 305. The flanges, including string 307, or the bushing 301 in its entirety consists of an elastic material, e.g. rubber or rubberlike plastics. Inside the bushing 301 there may be provided some kind of mechanism, for instance a one-way valve 309, or the bushing 301 may be constructed as a connection for connecting a hose or another conduit for gas or liquid. It is not necessary that the flanges 303 305 are elastic; they can be more or less rigid and be provided with bending scores allowing the flanges to be folded, or they may comprise a number of foldable flaps, which may overlap at adjacent edges when being folded.

In FIG. 4, the loading tube 201 is removed and the pincher 1 is in open configuration. In this configuration, the bushing 301 can be mounted on the mount point 109 of the inserter 101, and the string 307 of the bushing 301 may be connected to the pincher 1.

As the pincher is being closed, as can be seen in FIG. 5 where the pincher is in half-closed configuration, the pincher front flanges 303 of the bushing 301 will interact with the pincher 1 upon closing, in FIG. 5, with the springs 23 forming the walls of the bending section 13.

By further closing the pincher 1, the pincher front flanges 303 are forced to move radially inward. This results consequently in a longitudinally forward and radially inward movement of flange 303 forwarding it into the loading section 15, as depicted in FIG. 7. As the pincher 1 is closed, as can be seen in FIG. 5 where the pincher is in half-closed configuration, the pincher front flanges 303 of the bushing 301 will be bent forwards (i.e. bent away from the central cylindrical tube of the bushing 301) by the walls of the bending section 13, in FIG. 5 the springs 23. In closed configuration, the flange 303 has been bent forward it into the loading section 15, as depicted in FIG. 7.

Once the pincher 1 is closed, the inserter can be pushed 101 further in the insertion direction, the bushing 301 will be pushed into the loading section 215. The rear flanges 305 will abut against the wall 17 of the pincher 1, and will be forced to bend backwards, away from the insertion direction, and into the central axial passage 19. When the inserter 101 is pushed even further in the insertion direction, the whole bushing will be pushed into the loading section 215.

Alternatively, once the pincher 1 is closed, the loading tube 201 can be mounted on the pincher 1, as seen in FIG. 8. By pushing the inserter 101 further in the insertion direction, towards the delivery section 209 of the loading tube 201, the bushing 301 will be pushed into the delivery section 203 of the loading tube 201. The rear flanges 305 will abut against the wall 17 of the pincher 1, and will be forced to bend backwards, away from the insertion direction, and into the central axial passage 19. When the inserter 101 is pushed even further in the insertion direction, the bushing will be pushed into the loading tube 201.

Hence, the flanges 303, 305 are automatically bent into the described orientations by closing of the pincher 1. There is no need for manually squeezing/pushing/folding, or for performing similar mechanical tasks on any of the flanges 303 305 in order to load it into the loading section 215 or the loading tube 201. For facilitating displacement of the bushing 301 along the loading section 215 or loading tube 201, the latter may be pre-lubricated internally or coated with a suitable material on the interior surface thereof.

In order to introduce the bushing into an aperture in a flexible wall which is accessible from one side but not from the other side, the pincher 1 and the inserter 101 with the bushing 301 as a unit, is positioned so that the loading section 215 tip is reaching just inside the aperture.

The inserter 101 and the bushing 301 are pushed forward in the loading section 215, which is held stationary by the operator, so that front flange 303 will be located outside the loading section 215 tip, and inside the aperture. Thus, the front flange 303 is allowed to be unfolded on the inside of the wall. When this has taken place, the pincher 1 with the bushing 301 is withdrawn as a unit towards the opposite to the insertion direction, until the front flange 303 engages the inside of the wall. The pull applied to the pincher 1 possibly being so great that wall will be partly compressed. Due to anchoring by means of the anchoring security string 307 and also to some extent due to friction between the bushing 301 and the head 109, if any, the bushing 301 is prevented from sliding off the inserter 101. With the front flange 303 thus engaged with the inside of the wall, the pincher is further withdrawn over the inserter 101 in order to release also flange 305, so that it unfolds on the opposite wall side of the flexible wall.

If the loading device 1000 comprises a loading tube 201, the inserter 101 with the pincher 1 and loading tube 201 and the bushing 301 as a unit, is positioned so that the delivery section 209 tip is reaching just inside the aperture.

After having completed loading of the bushing 301 into the loading tube 201 as described above, the pincher 1 may optionally be removed from the inserter 101 and loading tube 201 by being slid backwards along the inserter 101, that is in the opposite direction of the loading direction, before the bushing 301 is introduced into the aperture.

The inserter 101 and the bushing 301 are pushed forward in the loading tube 201, which is held stationary by the operator, so that front flange 303 will be located outside the delivery section 209 tip of the loading tube 201, and inside the aperture. Thus, the front flange 303 is allowed to be unfolded on the inside of the wall. When this has taken place, the loading tube 201 with the bushing 301 is withdrawn as a unit towards the opposite to the insertion direction, until the front flange 303 engages the inside of the wall. The pull applied to the loading tube 201 possibly being so great that wall will be partly compressed. Due to anchoring by means of the anchoring security string 307 and also to some extent due to friction between the bushing 301 and the head 109, if any, the bushing 301 is prevented from sliding off the inserter 101. With the front flange 303 thus engaged with the inside of the wall, the loading tube 201 is further withdrawn over the inserter 101 in order to release also flange 305, so that it unfolds on the opposite wall side of the flexible wall.

The bushing is then to be uncoupled from the inserter, and the security string 307 cut. The pincher 1 or the loading tube 201 may be withdrawn completely from the inserter 101. The mount point 109 of the inserter 101 is disconnected from the bushing 301, which will then be left in wall with the flanges 303, 305 projecting around the aperture at opposite sides of the wall. Due to the flexible wall being compressed inbetween the flanges 303, 305 of the bushing 301, a tight and stable attachment of the bushing 301 in the wall will be secured. The anchoring security string 307 is cut off, and the mounting of the bushing 301 in the aperture is completed.

Hence, once the bushing 301 is mounted on the mount point 109 of an inserter 101 with mounted pincher 1, only one fluid motion of closing the pincher 1 is required to automatically bend the front flange 303 into the correct loading orientation. There is no need of holding or aligning individual pieces or worrying about positioning, since the pincher 1 will be correctly positioned by its mounting on the inserter 101.

By pushing the inserter 101 in the insertion direction, loading of the bushing 301 into the loading section 215 or loading tube 201 is automatically completed. After this, the pincher 1 may be removed. The pincher or loading tube 201 is then correctly positioned in relation to the aperture and held stationary by the operator, while the inserter 101 is pushed in the insertion direction until the front flange 303 will unfold on the inside of the wall. The loading tube 201 is withdrawn in order to unfold flange 305 on the opposite wall side of the flexible wall. Once the bushing is unmounted from the inserter 101 and the anchoring security string 307 is cut, the mounting of the bushing 301 in the aperture is completed.

Figure 12:
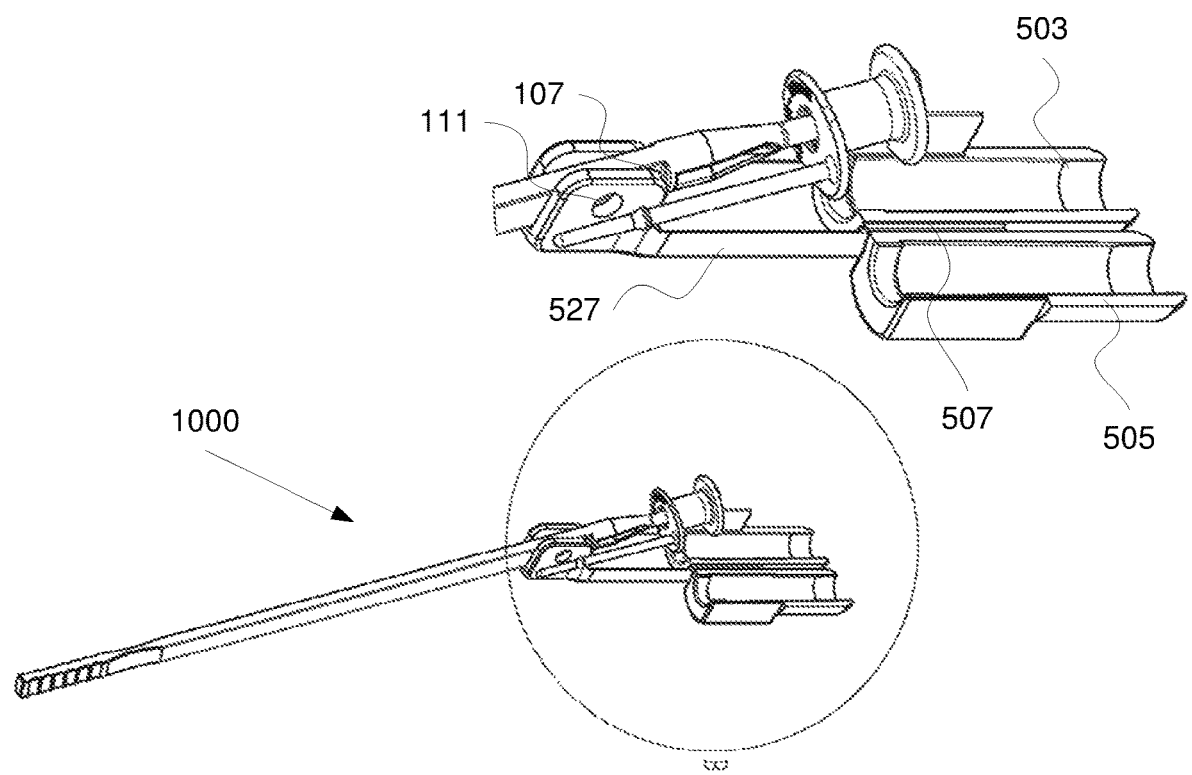
FIG. 12 shows a one schematic representation and one detailed view of a loading device in open configuration according to an embodiment of the invention, comprising an inserter where a bushing is mounted, and a pincher.
Figure 13:
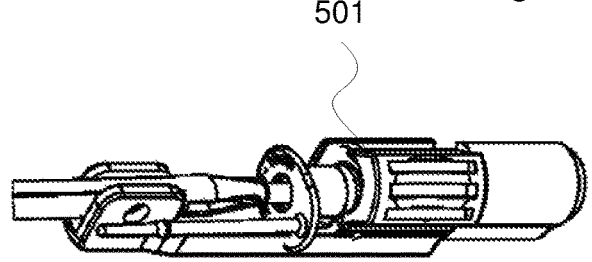
FIG. 13 shows two schematic representations illustrating a loading device in half-closed configuration according to an embodiment of the invention, comprising an inserter where a bushing is mounted, and a pincher.
Figure 13:
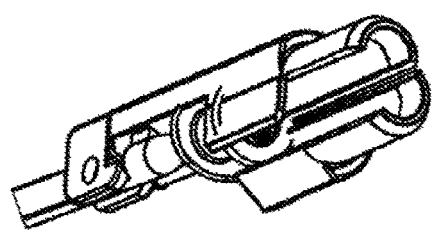

In an embodiment of the invention according to FIGS. 11 to 14, the pincher 501 comprises a first half 503 and a second half 505, are connected to each other at a hinge joint 507, parallel to the longitudinal direction of the loading device 1000. The pincher 501 is connected to the inserter at the groove portion 107 of the inserter 101 via a lever 527 connected to at least one of the halves 503 505, such as through the hole 111 of the inserter 101, as can be seen in FIG. 12. By enabling the lever 527 to rotate around its mount point at the groove portion 107, the pincher 501 can be rotated away from the inserter 101 mount portion 109 to facilitate mounting of the bushing 301, as can be seen in FIG. 12, while the pincher 501 can be rotated back and aligned with the longitudinal axis of the loading device 1000, as can be seen in FIG. 13, to be able to close around the mounted bushing 301.

Figure 14:
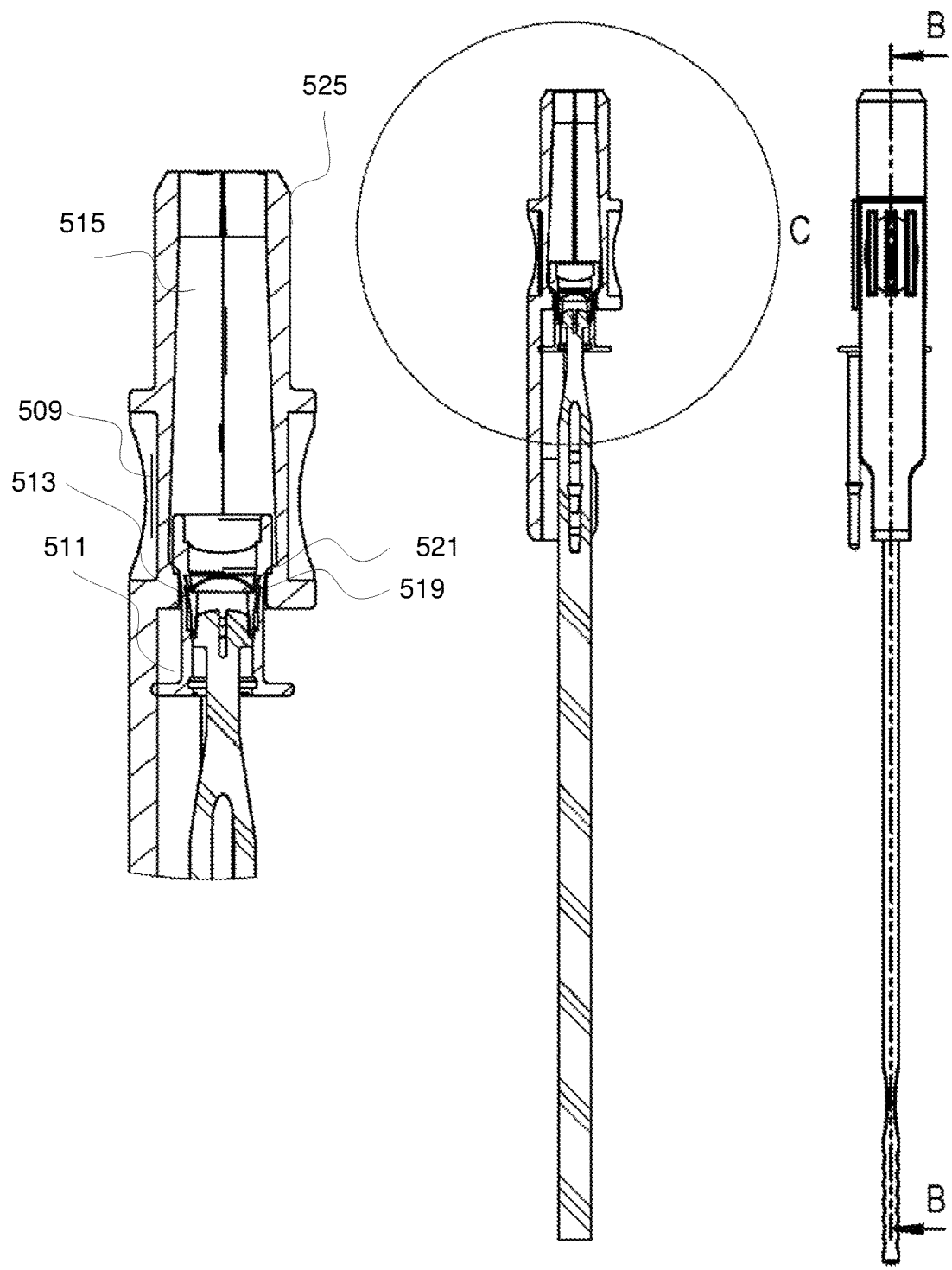
FIG. 14 shows one schematic representation, one cross-sectional view and one cross-sectional detailed view of a loading device in closed configuration according to an embodiment of the invention, comprising an inserter where a bushing is mounted, and a pincher.

The two halves 503, 505 may be rotated towards or away from each other, through rotation around the hinge joint 509, between a closed and open position, respectively. FIGS. 12 and 13 show the open configuration, while FIG. 14 shows the closed configuration. When in closed configuration, as can be seen in FIG. 14, the two halves form introduction section 511, a bending section 513 and a loading section 515 for the bushing 301.

The bending section 513 in-between the introduction section 511 and the loading section 515. The introduction section 511 comprises a wall 517 with a central axial passage 519 for receiving the bushing 301 towards the bending section 515 end. The bending section 513 comprises a central axis passage 519 with a diameter similar to that of the central section between the flanges 303, 305 of the bushing 301. The bending section 513 may have a tapered section 521 with a smaller inside diameter in the direction towards the introduction section 511 and a larger inside diameter at the loading section 515 end of bending section 513, as can be seen in FIG. 12. The angle of the tapered section 521 or springs facilitates easier bending of the flanges 303 of the bushing 301 by steering the bending of the flange 303 of a mounted bushing 301 to the correct bending direction. The loading section 515 has a central through-hole, with a diameter similar to that of the inside diameter of the introduction section 203 of the loading tube 201. When the loading tube 201 is mounted on the closed pincher 501, a continuous connection is formed from the loading section 515 to the loading tube 201.

The outer surface of the loading section 515 is a smooth cylindrical surface which functions as a tube mount 525 for the loading tube 201. Once the pincher 501 is in closed position, the loading tube 201 can easily be slid over the pincher tube mount 525.

Figure 15:
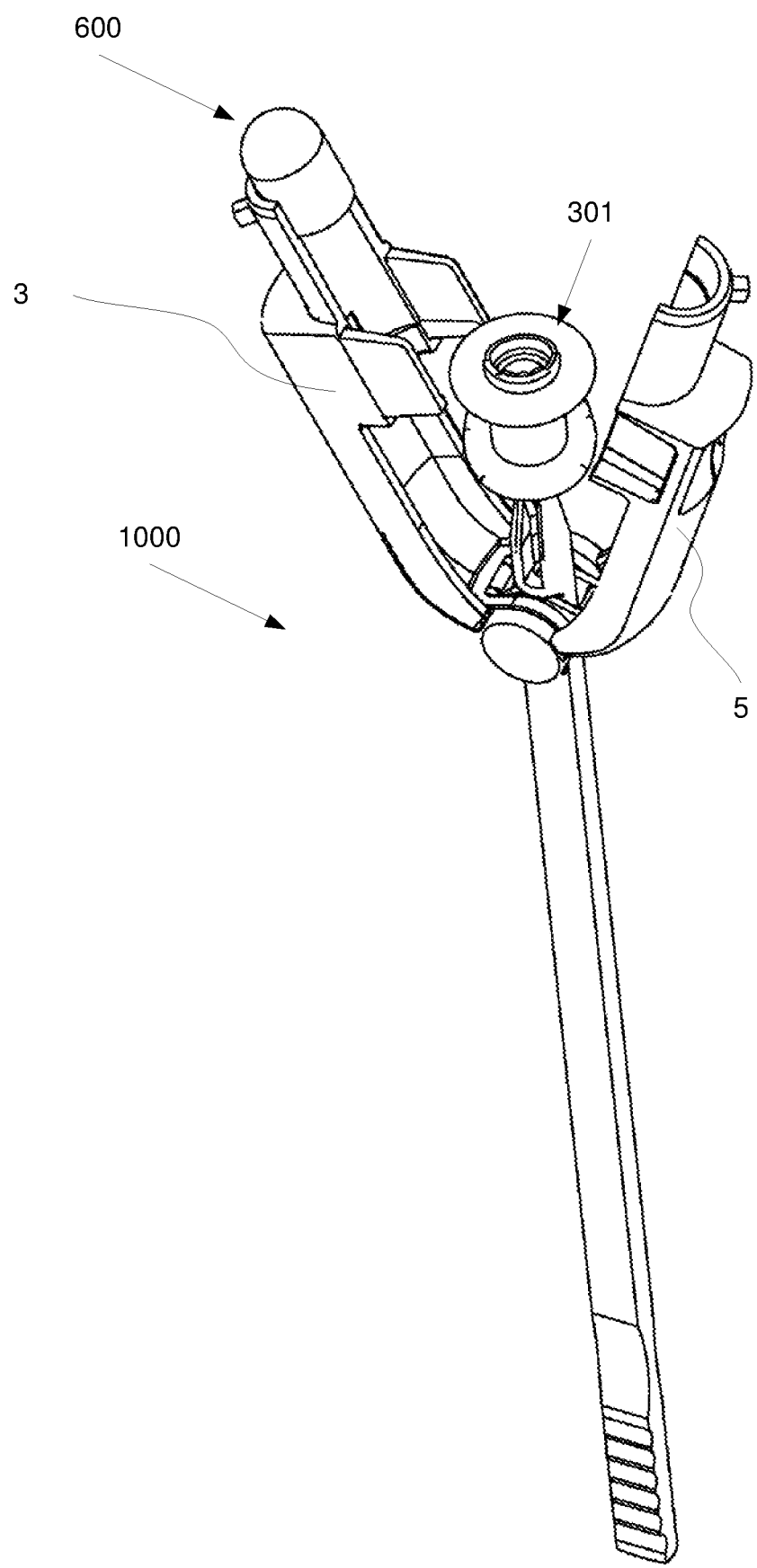
FIG. 15 shows one schematic perspective representation, of a loading device in according to an embodiment of the invention, wherein a bushing is to be inserted in a gel-cap.
Figure 16:
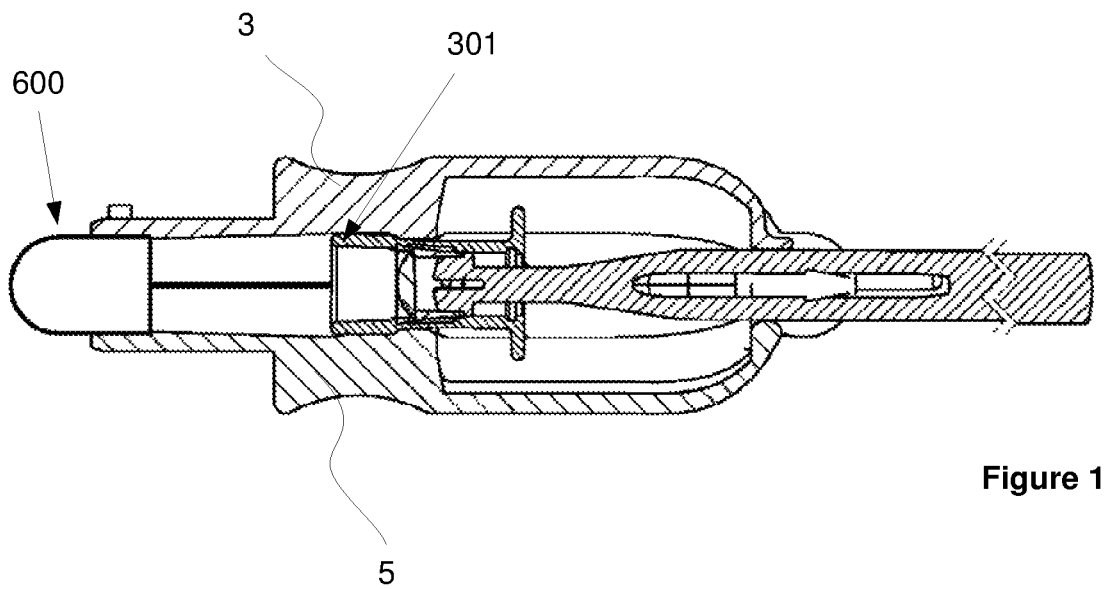
FIG. 16 shows one schematic cross-sectional representation, of a loading device in according to an embodiment of the invention, wherein a bushing is to be inserted in a gel-cap.
Figure 17:
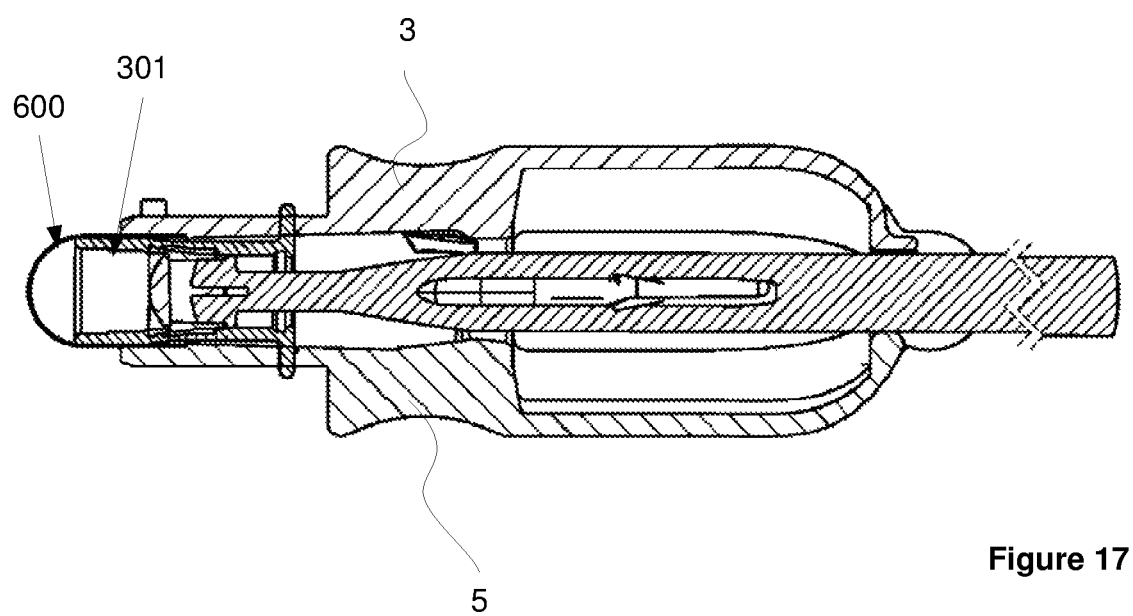
FIG. 17 shows one schematic cross-sectional representation, of a loading device in according to an embodiment of the invention, wherein a bushing is inserted in a gel-cap.

In FIGS. 15 to 17 it is disclosed how the loading device 1000 may be used in combination with a gel-cap 600 instead of a loading tube 201. The function of the gel-cap is to keep the distal end flange of the bushing 301, such as a voice prosthesis, folded distally, for introduction into a fistula in the oesophageal/tracheal wall.

The insertion of the esophageal flange of the voice prosthesis through the tracheoesophageal puncture can be aided by the use of the gel-cap 600. The oesophagal flange, i.e. the distal flange, of the voice prostesis, can then be placed within a dissolvable capsule (referred to herein as "gel-cap") to reduce the overall dimensions and facilitate the insertion through the tracheoesophageal puncture. Once in place, water or other liquid can be swallowed to dissolve the capsule and allow the esophageal flange to expand to its normal dimension and secure the voice prosthesis within the tracheoesophageal puncture.

Here, the gel-cap 600 may be arranged circumferentially of the two halves 3, 5 or, as shown in FIGS. 15 to 17, pinched between the two halves 3, 5, such that the outer surface area of the gel-cap 600 abuts the inner surface area of the two halves 3,5 in a retaining manner. Since the gel-cap 600 is to be introduced in the tracheoesophagal wall, such that the voice prosthesis, with gel-cap, is released when the insertion device is "relaxed", it is preferred to arrange the gel-cap 600 according to the latter, i.e. such that the gel-cap 600 abuts the inner surface area of the two halves 3,5 in a retaining manner. In this way, the voice prosthesis with gel-cap 600 may be separately inserted in the tracheoesophagal wall, after the voice prosthesis has been inserted into the gel-cap 600 through the use of the loading device 1000.

The elements of the loading device according to the invention may be provided in at least partly transparent material. In this case it is easily confirmed if the elements are correctly oriented in relation to each other, both during manufacturing and during insertion of the tubular element.

If the element to be mounted in a flexible wall, here the bushing 301, is constructed as a voice prosthesis, which is to be mounted in a fistula in the tracheoesophageal wall, said wall and fistula correspond to wall and aperture, respectively, in the illustrative examples.

The invention can be implemented in any suitable form within the scope of the appended claims. The elements and components of a embodiments of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and assemblies.

Although the present invention has been described above with reference to specific embodiments, it is not intended to be limited to the specific form set forth herein. Rather, the invention is limited only by the accompanying claims and, other embodiments than the specific above are equally possible within the scope of these appended claims, e.g. different bending means or tool forms than those described above.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A loading device for inserting a bushing into a through-aperture in a flexible wall or a cap, said bushing having flanges projecting transversely at each end thereof, said flanges being resiliently foldable towards the longitudinal axis of said bushing, said loading device comprising:
   an inserter having an inserter rod; and
   a pincher,
   wherein said inserter rod includes a distal bushing seat onto which the bushing can be mounted;
   wherein said pincher includes a first pincher half and a second pincher half, connected to each other at a hinge joint, wherein the first and the second pincher halves are configured to be pivoted between an open position and a closed position, and in the closed position, form an introduction section, a bending section and a loading section for the bushing on an inside of the first and second halves,
   wherein the pincher, mounted on the inserter, is configured to bend the flanges projecting transversely at each end of the bushing towards a longitudinal axis of the bushing mounted on the inserter rod, when the first and second halves are pivoted from an open configuration to a closed configuration that forms a continuous connection with the loading section;
   wherein, when the inserter is pushed distally in an insertion direction, the bushing is forced towards the loading section which will receive the bushing therein with said flanges folded and projecting substantially axially.

2. The loading device according to claim 1, further comprising a loading tube, wherein said pincher includes a tube mount for receiving a loading tube on the outside of the closed halves such that, when the inserter is pushed distally in an insertion direction, the bushing is forced towards the loading tube that is configured to receive the bushing therein with said flanges folded and projecting substantially axially.

3. The loading device according to claim 1, further comprising a gel-cap, wherein said pincher includes a cap mount for receiving the gel-cap on the outside or the inside of the closed halves such that, when the inserter is pushed distally in an insertion direction, the bushing is forced towards the gel-cap that is configured to receive the bushing therein with a distal end flange folded and projecting substantially axially.

4. The loading device according to claim 1, wherein the hinge joint is perpendicular to a central axis of the loading device.

5. The loading device according to claim 1, wherein the hinge joint is parallel to the central axis of the loading device.

6. The loading device according to claim 1, wherein the pincher comprises at least one spring in the bending section.

7. The loading device according to claim 1, wherein the bushing during insertion thereof is held at a security string projecting from said bushing.

8. The loading device according to claim 1, wherein said bushing is voice prosthesis, said flexible wall is a tracheoesophageal wall and said through-aperture is a fistula in the tracheoesophageal wall.

9. A loading device for inserting a bushing having flanges into a through-aperture in a flexible wall or a cap, the loading device comprising:
   an inserter having an inserter rod including a distal bushing seat; and
   a pincher mounted on the inserter rod, the pincher including a hinge joint, a first pincher half and a second pincher half, wherein the first and the second halves are configured to be pivoted between an open position and a closed position, the closed position forming an introduction section, a bending section and a loading section,
   wherein the pincher is configured to bend the flanges towards a longitudinal axis of the bushing mounted on the inserter rod, when the first and second pincher halves are pivoted from an open configuration to a closed configuration that forms a continuous connection with the loading section;
   wherein, when the inserter is pushed distally in an insertion direction, the bushing is forced towards the loading section that is configured to receive the bushing therein with said flanges folded and projecting substantially axially.

10. The loading device according to claim 9, further comprising a loading tube, wherein said pincher includes a tube mount for receiving a loading tube on the outside of the closed halves such that when the inserter is pushed distally in an insertion direction, the bushing is forced towards the loading tube that is configured to receive the bushing therein with said flanges folded and projecting substantially axially.

11. The loading device according to claim 9, further comprising a gel-cap, wherein said pincher includes a cap mount for receiving the gel-cap on the outside or the inside of the closed halves such that, when the inserter is pushed distally in an insertion direction, the bushing is forced towards the gel-cap that is configured to receive the bushing therein with a distal end flange folded and projecting substantially axially.

12. The loading device according to claim 9, wherein the hinge joint is perpendicular to a central axis of the loading device.

13. The loading device according to claim 9, wherein the hinge joint is parallel to the central axis of the loading device.

14. The loading device according to claim 9, wherein the pincher includes at least one spring in the bending section.

15. The loading device according to claim 9, wherein the bushing during insertion thereof is held at a security string projecting from said bushing.

16. The loading device according to claim 9, wherein said bushing is voice prosthesis, said flexible wall is a tracheoesophageal wall and said through-aperture is a fistula in the tracheoesophageal wall.

* * * * *